United States Patent
Moltzen et al.

(10) Patent No.: US 6,921,774 B2
(45) Date of Patent: Jul. 26, 2005

(54) COMPOUNDS AND THEIR USE AS GLYCINE TRANSPORT INHIBITORS

(75) Inventors: Ejner Knud Moltzen, Gentofte (DK); Paul Garrick Smith, Valby (DK); Christian Krog-Jensen, Rungsted Kyst (DK); Klaus Peter Bøgesø, Hørsholm (DK)

(73) Assignee: H. Lundbeck A/S, Copenhagen-Valby (DK)

( * ) Notice: Subject to any disclaimer, the term of this patent is extended or adjusted under 35 U.S.C. 154(b) by 0 days.

(21) Appl. No.: 10/348,490

(22) Filed: Jan. 17, 2003

(65) Prior Publication Data

US 2003/0181445 A1 Sep. 25, 2003

Related U.S. Application Data

(63) Continuation of application No. PCT/DK01/00510, filed on Jul. 19, 2001.

(30) Foreign Application Priority Data

Jul. 21, 2000 (DK) ........................ 2000 01124

(51) Int. Cl.[7] ...................... A61K 31/34; A61K 31/195; C07C 229/36; C07D 307/87; C07D 333/72
(52) U.S. Cl. ...................... 514/443; 514/469; 514/517; 514/530; 514/563; 514/620; 549/6; 549/58; 549/220; 549/345; 549/467; 558/166; 562/48; 562/104; 562/428; 562/443; 562/444; 564/164; 560/38
(58) Field of Search ....................... 560/38, 39; 562/48, 562/104, 428, 443, 444; 549/58, 345, 467, 6, 220, 462; 558/166; 564/164; 514/443, 469, 517, 530, 563, 620

(56) References Cited

U.S. PATENT DOCUMENTS

| 3,549,656 A | 12/1970 | Petersen et al. |
| 4,136,193 A | 1/1979 | Bøgesø et al. |
| 6,566,550 B2 * | 5/2003 | Lowe, III .................. 562/443 |

FOREIGN PATENT DOCUMENTS

| EP | 0 502 845 B1 | 8/1977 |
| GB | 1166711 | 10/1969 |
| WO | WO 93/10228 | 5/1993 |
| WO | WO 97/45446 | 12/1997 |
| WO | WO 98/46619 | 10/1998 |
| WO | WO 00/34263 | 6/2000 |
| WO | WO 01/03694 A1 | 1/2001 |

OTHER PUBLICATIONS

Maurer, Hans H. et al., Screening Procedure for Detection of Antidepressants of the Selective Serotonin Reuptake Inhibitor Type and their Metabolites in Urine as Part of a Modified Systematic Toxicological Analysis Procedure using Gas Chromatography–Mass Spectrometry, *Journal of Analytical Toxicology* 24, 340–347 (2000).

Bergeron, Richard et al., Modulation of N–methyl–D–aspartate receptor function by glycine transport, *Proc. Natl. Acad. Sci.* 95, 15730–15734 (1998).

Supplisson, Stephane et al., Control of NMDA Receptor Activation by a Glycine Transporter Co–Expressed in *Xenopus* Oocytes, *The Journal of Neuroscience* 17(12), 4580–4590 (1997).

Javitt, Daniel C. et al., Reversal of Phencyclidine–Induced Hyperactivity by Glycine and the Glycine Uptake Inhibitor Glycyldodecylamide, *Neuropsychopharmacology* 17(3), 202–204 (1997).

Borden, Laurence A, et al., Glycine Transport Inhibitors: A New Class of Antipsychotics? *Schizophrenia Research* 24(1–2), 211 (1997).

STN International, file CAPLUS, CAPLUS accession No. 1970:90271, document No. 72:90271, Kefalas A/S (May 12, 1984).

Fjalland, B. et al., Anti–Nociceptive Activity of Some Thiophthalenes with Morphine–like Properties, *Acta pharmacologtica* 32(3–4), 278–284 (1973).

Bhatt, M.V. et al., Aspects of Tautomerism. Part II. + Reactions of the Pseudo–acid Chloride of o–Benzoylbenzoic Acid with Nucleophiles, *J. Chem. So. (C)*, 1772–1777 (1971).

Matier, W.L. et al., Novel Cyclizations and Ring–Opening Reactions of 3–Phenylindene Derivatives, *J. Org. Chem.* 36(5), 650–654 (1971).

* cited by examiner

Primary Examiner—Bernard Dentz
(74) *Attorney, Agent, or Firm*—Darby & Darby

(57) ABSTRACT

The invention provides novel compounds of the formula I below:

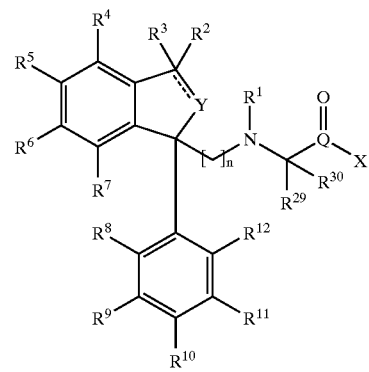

wherein the meaning of each substituent is defined in the application. The compounds are useful as inhibitors of the glycine transporter and useful in the treatment of diseases responsive to the inhibition of the glycine transporter. The invention provides a pharmaceutical composition comprising a compound of Formula I as defined above and the use of compounds as above for the manufacture of medicaments for treatment of diseases responsive to ligands of the glycine transporter.

20 Claims, No Drawings

COMPOUNDS AND THEIR USE AS GLYCINE TRANSPORT INHIBITORS

This application is a continuation of international application Serial Number PCT/DK01/00510 filed Jul. 19, 2001.

The present invention provides novel compounds of the general formula I, and their use as glycine transport inhibitors.

BACKGROUND OF THE INVENTION

Glutamic acid is the major excitatory amino acid in the mammalian central nervous system (CNS), and acts through two classes of receptors the ionotropic and metabotrobic receptors respectively. The ionotropic glutamate receptors are divided into three subtypes based on the affinities of agonists for these receptors, namely N-methyl-D-aspartate (NMDA), (R,S)-2-amino-3-(3-hydroxy-5-methylisoxazol-4-yl)propanoic acid (AMPA) and kainic acid (or kainate) receptors.

The NMDA receptor contains binding sites for modulatory compounds such as glycine and polyamines. Binding of glycine to its receptor enhances the NMDA receptor activation. Such NMDA receptor activation may be a potential target for the treatment of schizophrenia and other diseases linked to NMDA receptor dysfunction. An activation can be achieved by an inhibitor of the glycine transporter.

Molecular cloning has revealed the existence of two types of glycine receptors, GlyT-1 and GlyT-2, wherein GlyT-1 can be further subdivided into GlyT-1a, GlyT-1b and GlyT-1c. The NMDA receptor is blocked by compounds such as phencyclidine which induce a psychotic state which resembles schizophrenia. Likewise, the NMDA antagonists, such as ketamine, induce negative and cognitive symptoms similar to schizophrenia. This indicates that NMDA receptor dysfunction is involved in the pathophysiology of schizophrenia. The NMDA receptor has been associated with a number of diseases, such as pain (Yaksh *Pain* 1989, 37, 111–123), spasticity, myuoclonus and epilepsy (Truong et. al. *Movement Disorders* 1988, 3, 77–87), learning and memory (Rison et. al. *Newrosci. Biobehav. Rev.* 1995, 19, 533–552,).

Thus, glycine transporter antagonistists or inhibitors are believed to be highly beneficial in the treatment of schizophrenia, including both the positive and the negative symptoms of schizophrenia, other psychoses, dementia, and improving cognition in conditions where the cognitive processes are diminished, i.e. Alzheimer's disease, multi-infarct dementia, AIDS dementia, Huntington's disease, Parkinson's disease, amyotrophic lateral sclerosis or diseases wherein the brain is damaged by inner or outer influence, such as trauma to the head or stroke.

Clinical trials with glycine have been reported (Javitt et. al. *Am. J. Psychiatry* 1994, 151, 1234–1236), (Leiderman et. al. *Biol. Psychiatry* 1996, 39, 213–215). The treatment with high-dose glycine is reported to improve the symptoms of schizophrenia. There is a need for more efficient compounds as ligands for the glycin transporter for the treatment of NMDA associated diseases.

The compounds of the present invention are potent ligands for the glycine transporter.

SUMMARY OF THE INVENTION

The invention provides novel compounds of the formula I below:

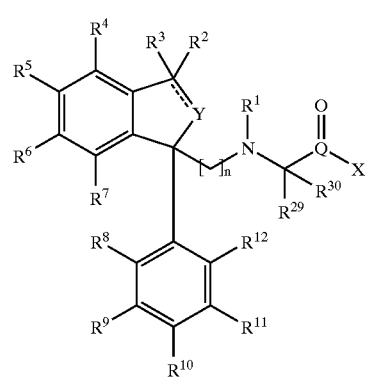

wherein $R^1$ represents hydrogen, $C_{1-6}$-alkyl, cycloalkyl or cycloalkylalkyl;

$R^2$ and $R^3$ independently represent hydrogen, halogen, $C_{1-6}$-alkyl, $C_{3-8}$ cycloalkyl or $C_{3-8}$ cycloalkyl-$C_{1-6}$-alkyl or $R^2$ and $R^3$ together form a $C_{3-8}$-cycloalkyl;

$R^4$, $R^5$, $R^6$ and $R^7$ independently represent hydrogen, halogen, $CF_3$, $NO_2$, $CN$, $C_{1-6}$ alkyl, $C_{2-6}$ alkenyl, $C_{2-6}$ alkynyl, $C_{3-8}$ cycloalkyl, $C_{1-6}$ alkoxy, $C_{1-6}$ alkylthio, $OH$, $SH$, $NR^{14}R^{15}$, wherein $R^{14}$ and $R^{15}$ independently represent hydrogen or $C_{1-6}$-alkyl; —$COR^{16}$ wherein $R^{16}$ represents $OH$, $C_{1-6}$-alkyl, $C_{1-6}$-alkoxy, $NR^{17}R^{18}$, wherein $R^{17}$ and $R^{18}$ independently represent hydrogen or $C_{1-6}$-alkyl; aryl or heteroaryl, wherein aryl and heteroaryl are optionally substituted one or more times with halogen, $CF_3$, $OCF_3$, $CN$, $NO_2$, $C_{1-6}$ alkyl, $C_{2-6}$ alkenyl, $C_{2-6}$ alkynyl, $C_{3-8}$ cycloalkyl, $C_{1-6}$ alkoxy, $C_{1-6}$ thioalkyl, $OH$, $SH$ or $NR^{24}R^{25}$, wherein $R^{24}$ and $R^{25}$ independently represent hydrogen or $C_{1-6}$-alkyl;

or $R^4$ and $R^5$, or $R^5$ and $R^6$, or $R^6$, and $R^7$ together form a fused, aromatic, saturated or partly saturated ring which optionally contains one or more heteroatoms such as O, N or S;

$R^8$, $R^9$, $R^{10}$, $R^{11}$ and $R^{12}$ independently represent hydrogen, halogen, $CF_3$, $OCF_3$, $CN$, $NO_2$, $C_{1-6}$ alkyl, $C_{2-6}$ alkenyl, $C_{2-6}$ alkynyl, $C_{3-8}$ cycloalkyl, $C_{1-6}$ alkoxy, $C_{1-6}$-alkylthio, $OH$, $SH$, $NR^{19}R^{20}$, wherein $R^{19}$ and $R^{20}$ independently represent hydrogen or $C_{1-6}$-alkyl; or $R^8$, $R^9$, $R^{10}$, $R^{11}$ and $R^{12}$ independently represent —$COR^{21}$, wherein $R^{21}$ represents $OH$, $C_{1-6}$-alkoxy, $NR^{22}R^{23}$, wherein $R^{22}$ and $R^{23}$ independently represent hydrogen or $C_{1-6}$-alkyl; or $R^8$, $R^9$, $R^{10}$, $R^{11}$, and $R^{12}$ independently represent aryl or heteroaryl, wherein aryl and heteroaryl are optionally substituted one or more times with halogen, $CF_3$, $OCF_3$, $CN$, $NO_2$, $C_{1-6}$ alkyl, $C_{2-6}$ alkenyl, $C_{2-6}$ alkynyl, $C_{3-8}$ cycloalkyl, $C_{1-6}$ alkoxy, $C_{1-6}$ alkythio, $OH$, $SH$, $COR^{26}$, wherein $R^{26}$ represents $OH$, $C_{1-6}$ alkoxy or $C_{1-6}$ alkyl; or $NR^{30}R^{31}$, wherein $R^{30}$ and $R^{31}$ independently represent hydrogen or $C_{1-6}$-alkyl;

$R^8$ and $R^9$, or $R^9$ and $R^{10}$, or $R^{10}$ and $R^{11}$, or $R^{11}$ and $R^{12}$ together form a fused, aromatic, saturated or partly saturated ring which optionally contains one or more heteroatoms such as O, N, or S;

Y is O, S, $CH_2$ or CH, and when Y is CH then the dotted line is a bond;

n is 2, 3, 4, 5 or 6;

Q represents C, P—$OR^{29}$, or S=O, wherein $R^{29}$ represents hydrogen or $C_{1-6}$-alkyl;

X is $OR^{13}$ or $NR^{27}R^{28}$, wherein $R^{13}$, $R^{27}$, and $R^{28}$ independently represent hydrogen, $C_{1-6}$-alkyl, aryl or aryl-$C_{1-6}$-alkyl, wherein aryl may be substituted with halogen, CF$_3$, OCF$_3$, CN, NO$_2$, or C$_{1-6}$ alkyl; optionally R$^{27}$ and R$^{28}$ together form a ring which may contain further nitrogen, oxygen or sulfur atoms and the ring may optionally be partly saturated;

R$^{29}$ and R$^{30}$ represent hydrogen, C$_{1-6}$-alkyl, cycloalkyl or cycloalkylalkyl or a pharmaceutically acceptable addition salt thereof;

The compounds are useful as inhibitors of the glycine transporter and useful in treatment of diseases responsive to the inhibition of the glycine transporter.

DETAILED DESCRIPTION OF THE INVENTION

In a preferred embodiment of the invention, Q is C;

Other preferred embodiments are wherein n is 2 or 3;

Another preferred embodiment is wherein R$^1$ is CH$_3$;

Yet another preferred embodiment is wherein X is OH or C$_{1-6}$-alkoxy; more preferred is wherein X is OH, OCH$_3$ or OC$_2$H$_5$ Other preferred embodiments are wherein R$^7$ represent hydrogen, and R$^4$, R$^5$ or R$^6$ represent hydrogen, CN, halogen, C$_{1-6}$-alkyl, CF$_3$ or phenyl optionally substituted one or more times with halogen, C$_{1-6}$-alkyl, C$_{1-6}$-alkoxy, CF$_3$, or R$^4$, R$^5$ or R$^6$ represent heteroaryl optionally substituted one or more times with halogen, or wherein R$^4$ and R$^5$ or R$^5$ and R$^6$ together form a fused aryl;

Another preferred embodiment of the invention is wherein R$^8$, R$^9$, R$^{10}$, R$^{11}$ or R$^{12}$ independently represent hydrogen, halogen, C$_{1-6}$-alkyl, C$_{1-6}$-alkoxy, or R$^8$ and R$^9$ or R$^9$ and R$^{10}$ together form a fused aryl;

In an more preferred embodiment, one or two of R$^8$, R$^9$, R$^{10}$, R$^{11}$ or R$^{12}$ represent halogen, C$_{1-6}$-alkyl, CF$_3$ or C$_{1-6}$-alkoxy;

In a more preferred embodiment of the invention R$^4$, R$^6$, R$^7$, R$^8$, R$^9$ and R$^{12}$ are all hydrogen and R$^5$ represents halogen, CF$_3$, CN, C$_{1-6}$ alkyl, C$_{1-6}$ alkoxy or —COR$^{16}$, wherein R$^{16}$ represents C$_{1-6}$-alkyl; and R$^{10}$ and R$^{11}$ represent hydrogen, halogen, CF$_3$, or CN, provided that at least one of R$^{10}$ and R$^{11}$ is not hydrogen;

R$^{29}$ and R$^{30}$ independently represent hydrogen or C$_{1-6}$-alkyl or R$^2$ and R$^3$ together form a C$_{3-8}$-cycloalkyl;

Another preferred embodiment of the invention is wherein the compounds are the following N-{3-[5-Cyano-1-(4-fluorophenyl)-1,3-dihydroisobenzofuran-1-yl]-1-propyl}glycine ethyl ester, N-{3-[5-Cyano-1-(4-fluorophenyl)-1,3-dihydroisobenzofuran-1-yl]-1-propyl}-N-methylglycine ethyl ester, N-{3-[5-Cyano-1-(4-fluorophenyl)-1,3-dihydroisobenzofuran-1-yl]-1-propyl}glycine, N-{3-[5-Cyano-1-(4-fluorophenyl)-1,3-dihydroisobenzofuran-1-yl]-1-propyl}-N-methylglycine, N-{3-[1-(3-chlorophenyl)-1,3-dihydroisobenzofuran-1-yl]-1-propyl}-N-methylglycine, N-{3-[1-(3-trifluoromethylphenyl)-1,3-dihydroisobenzofuran-1-yl]-1-propyl}-N-methylglycine, N-{3-[1-(3-trifluoromethylphenyl)-1,3-dihydroisobenzofuran-1-yl]-1-propyl}-N-methyl(1-ethyl)glycine, N-{3-[1-(4-methylphenyl)-1,3-dihydroisobenzofuran-1-yl]-1-propyl}-N-methylglycine, N-{3-[1-(4-fluorophenyl)-1,3-dihydroisobenzofuran-1-yl]-1-propyl}-N-methylglycine, N-{3-[1-(4-fluorophenyl)-1,3-dihydroisobenzofuran-1-yl]-1-propyl}-N-methylalanine, N-{3-[1-(4-fluorophenyl)-1,3-dihydroisobenzofuran-1-yl]-1-propyl}-N-methyl(1-ethyl)glycine, N-{3-[4-chloro-1-(3-methyl-4-fluorophenyl)-1,3-dihydroisobenzofuran-1-yl]-1-propyl}-N-methylglycine, N-{3-[4-chloro-1-(4-chlorophenyl)-1,3-dihydroisobenzofuran-1-yl]-1-propyl}-N-methylglycine, N-{3-[5-chloro-1-(4-chlorophenyl)-1,3-dihydroisobenzofuran-1-yl]-1-propyl}-N-methylalanine, N-{3-[6-chloro-1-(3-methyl-4-fluorophenyl)-1,3-dihydroisobenzofuran-1-yl]-1-propyl}-N-methylglycine, N-{3-[6-chloro-1-(4-chlorophenyl)-1,3-dihydroisobenzofuran-1-yl]-1-propyl}-N-methylglycine, N-{3-[6-chloro-1-(4-methylphenyl)-1,3-dihydroisobenzofuran-1-yl]-1-propyl}-N-methylglycine, N-{3-[6-chloro-1-(4-methoxyphenyl)-1,3-dihydroisobenzofuran-1-yl]-1-propyl}-N-methylglycine, N-{3-[5-fluoro-1-(4-chlorophenyl)-1,3-dihydroisobenzofuran-1-yl]-1-propyl}-N-methylglycine, N-{3-[5-fluoro-1-(4-methoxyphenyl)-1,3-dihydroisobenzofuran-1-yl]-1-propyl}-N-methylglycine, N-{3-[5-trifluoromethyl-1-(4-fluorophenyl)-1,3-dihydroisobenzofuran-1-yl]-1-propyl}-N-methylglycine, N-{3-[5-trifluoromethyl-1-(4-fluorophenyl)-1,3-dihydroisobenzofuran-1-yl]-1-propyl}-N-methylalanine, N-{3-[5-cyano-1-(3-methyl-4-fluorophenyl)-1,3-dihydroisobenzofuran-1-yl]-1-propyl}-N-methylglycine, N-{3-[5-cyano-1-(4-cyanophenyl)-1,3-dihydroisobenzofuran-1-yl]-1-propyl}-N-methylalanine, N-{3-[5-cyano-1-(4-methoxyphenyl)-1,3-dihydroisobenzofuran-1-yl]-1-propyl}-N-methylglycine, N-{3-[5-cyano-1-(4-fluorophenyl)-1,3-dihydroisobenzofuran-1-yl]-1-propyl}-N-methylglycine, N-{2-[5-cyano-1-(4-fluorophenyl)-1,3-dihydroisobenzofuran-1-yl]ethyl}-N-methylglycine, N-{3-[5-Chloro-1-(4-chloro-phenyl)-indan-1-yl]-propyl}-N-methylglycine, N-{3-[5-Chloro-1-(4-chloro-phenyl)-indan-1-yl]-propyl}-N-methylalanine, N-{3-[3-cyclo-1-(4-methylphenyl)-1,3-dihydroisobenzofuran-1-yl]-1-propyl}-N-methylglycine, N-[3-(3,3-Dimethyl-1-phenyl-1,3-dihydro-benzo[c]thiophen-1-yl)-propyl]-N-methylglycine, N-[3-(3,3-Dimethyl-1-phenyl-1,3-dihydro-benzo[c]thiophen-1-yl)-propyl]-N-methylalanine, N-{3-[1-(4-Fluoro-phenyl)-3-dimethyl-1,3-dihydro-isobenzofuran-1-yl]-propyl}-N-methylglycine, N-{3-[5-Bromo-1-(4-chlorophenyl)-1,3-dihydroisobenzofuran-1-yl]-1-propyl}-N-methylglycine, N-{2-[1-(4-Chloro-phenyl)-3,3-dimethyl-1,3-dihydro-isobenzofuran-1-yl]-ethyl}-N-methylglycine, N-[3-(3-methyl-1-phenyl-1H-inden-1-yl)-propyl]-N-methylglycine, N-[3-(5-Chloro-1-thiophen-2-yl-1,3-dihydro-isobenzofuran-1-yl)-propyl]-N-methylglycine, N-[3-(5-Chloro-1-thiophen-2-yl-1,3-dihydro-isobenzofuran-1-yl)-propyl]-N-methyl(1-ethyl)-glycine, N-[3-(3-methyl-1-phenyl-1,3-dihydro-isobenzofuran-1-yl)-propyl]-N-methylalanine, N-[3-(3-methyl-1-phenyl-1,3-dihydro-isobenzofuran-1-yl)-propyl]-N-methyl(1-ethyl)-glycine, N-[3-(3,3-Dimethyl-1-phenyl-1,3-dihydro-isobenzofuran-1-yl)-ethyl]-N-methylalanine, N-[3-(3,3-Dimethyl-1-(4-fluoro-phenyl)-1,3-dihydro-isobenzofuran-1-yl)-ethyl]-N-methylalanine, N-[3-(3,3-Dimethyl-1-phenyl-1,3-dihydro-isobenzofuran-1-yl)-ethyl]-N-methyl-(1-ethyl)glycine, N-[3-(3,3-Dimethyl-1-(4-fluoro-phenyl)-1,3-dihydro-isobenzofuran-1-yl)-ethyl]-N-methyl-(1-ethyl)glycine, N-[3-(3,3-Diethyl-1-phenyl-1,3-dihydro-isobenzofuran-1-yl)-propyl]-N-methylalanine, N-[3-(3,3-Diethyl-1-(4-chloro-phenyl)-1,3-dihydro-isobenzofuran-1-yl)-propyl]-N-methylalanine,
N-[3-(3,3-Diethyl-1-(4-chloro-phenyl)-1,3-dihydro-isobenzofuran-1-yl)-propyl]-N-methylglycine,
N-[3-(1-phenyl-1,3-dihydro-benzo[c]thiophen-1-yl)-propyl]-N-methylalanine,
N-{3-[1-(4-Chloro-phenyl)-3,3-dimethyl-indan-1-yl]-propyl}-N-methylglycine,
N-{3-[1-(4-Chloro-phenyl)-3,3-diethyl-1,3-dihydro-isobenzofuran-1-yl]-propyl}-N-methyl-alanine,
N-[2-(3-methyl-1-phenyl-indan-1-yl)-ethyl]-amino}-N-methyl alanine,
N-[3-(1-phenyl-(1H)-inden-1-yl)-propyl]-N-methyl-alanine,
N-{3-[1-(4-Fluoro-phenyl)-5-(4-trifluoromethyl-phenyl)-1,3-dihydro-isobenzofuran-1-yl]-propyl}-N-methyl-glycine,
N-{3-[5-Chloro-1-(4-chloro-phenyl)-indan-1-yl]-propyl}-N-methyl-glycine,
N-{3-[5-Chloro-1-(4-chloro-phenyl)-indan-1-yl]-propyl}-N-methyl-alanine,
N-{3-[1-(4-chloro-phenyl)-5-(4-trifluoromethyl-phenyl)-1,3-dihydro-isobenzofuran-1-yl]-ethyl}-N-methyl-glycine,
N-{3-[1-(4-Chloro-phenyl)-5-(4-methyl-phenyl)-1,3-dihydro-isobenzofuran-1-yl]-ethyl}-N-methyl-glycine,
N-{3-[1-(4-Chloro-phenyl)-5-(4-methoxy-phenyl)-1,3-dihydro-isobenzofuran-1-yl]-ethyl}-N-methyl-glycine,
N-{3-[1-(4-Chloro-phenyl)-5-(2-thiophenyl)-1,3-dihydro-isobenzofuran-1-yl]-ethyl}-N-methyl-glycine,
N-{3-[1-(4-Chloro-phenyl)-5-(4-methyl-phenyl)-1,3-dihydro-isobenzofuran-1-yl]-propyl}-N-methyl-glycine,
N-{3-[1-(4-Chloro-phenyl)-5-(4-methoxy-phenyl)-1,3-dihydro-isobenzofuran-1-yl]-propyl}-N-methyl-glycine,
N-{3-[1-(4-chloro-phenyl)-5-(4-trifluoromethyl-phenyl)-1,3-dihydro-isobenzofuran-1-yl]-propyl}-N-methyl-glycine,
N-{3-[1-(4-Chloro-phenyl)-5-(4-chloro-phenyl)-1,3-dihydro-isobenzofuran-1-yl]-ethyl}-N-methyl-glycine,
N-{2-[1-(4-Chloro-phenyl)-5-(5-chloro-thiophen-2-yl)-1,3-dihydro-isobenzofuran-1-yl]-ethyl}-N-methyl-glycine,
N-{3-[1-(4-Chloro-phenyl)-5-(3-methyl-phenyl)-1,3-dihydro-isobenzofuran-1-yl]-ethyl}-N-methyl-glycine,
N-{3-[1-(4-Chloro-phenyl)-5-(2-methyl-phenyl)-1,3-dihydro-isobenzofuran-1-yl]-ethyl}-N-methyl-glycine,
N-{3-[1-(4-Chloro-phenyl)-5-(2,5-dichloro-phenyl)-1,3-dihydro-isobenzofuran-1-yl]-ethyl}-N-methyl-glycine,
N-{3-[1-(4-chloro-phenyl)-5-(3-trifluoromethyl-phenyl)-1,3-dihydro-isobenzofuran-1-yl]-ethyl}-N-methyl-glycine,
N-{3-[1-(4-chloro-phenyl)-5-(3-trifluoromethyl-phenyl)-1,3-dihydro-isobenzofuran-1-yl]-propyl}-N-methyl-glycine,
N-{3-[1-(4-Chloro-phenyl)-5-(3,4-dichloro-phenyl)-1,3-dihydro-isobenzofuran-1-yl]-ethyl}-N-methyl-glycine,
N-{3-[1-(4-Chloro-phenyl)-5-(4-chloro-phenyl)-1,3-dihydro-isobenzofuran-1-yl]-propyl}-N-methyl-glycine,
N-{3-[1-(4-Chloro-phenyl)-5-(3-methyl-phenyl)-1,3-dihydro-isobenzofuran-1-yl]-propyl}-N-methyl-glycine,
N-{3-[1-(4-Chloro-phenyl)-5-(2-methyl-phenyl)-1,3-dihydro-isobenzofuran-1-yl]-propyl}-N-methyl-glycine,
N-{3-[1-(4-Chloro-phenyl)-5-(2,5-dichloro-phenyl)-1,3-dihydro-isobenzofuran-1-yl]-propyl}-N-methyl-glycine,
N-{3-[1-(4-Chloro-phenyl)-5-(3,4-dichloro-phenyl)-1,3-dihydro-isobenzofuran-1-yl]-propyl}-N-methyl-glycine,
N-{3-[1-(4-chloro-phenyl)-5-(2-trifluoromethyl-phenyl)-1,3-dihydro-isobenzofuran-1-yl]-propyl}-N-methyl-glycine,
or a pharmaceutically acceptable addition salt thereof.

The invention provides a pharmaceutical composition comprising at least one compound of Formula I as defined above or a pharmaceutically acceptable acid addition salt thereof in a therapeutically effective amount and in combination with one or more pharmaceutically acceptable carriers or diluents.

The invention also provides the use of compounds as above for the manufacture of medicaments for treatment of diseases responsive to ligands of the glycine transporter.

The invention provides a method for treatment of diseases responsive to ligands of the glycine transporter.

In preferred embodiments of the invention, the ligands are antagonists of the glycine transporter.

Pharmaceutically acceptable addition salts are those which form pharmcological acceptable anions such as maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic and theophylline acetic acids, as well as the 8-halotheophyllines, for example 8-bromotheophylline. Exemplary of such inorganic salts are those with hydrochloric, hydrobromic, sulfuric, sulfamic, phosphoric and nitric acids.

The compound of the invention may be administered in any suitable way such as orally or parenterally, and it may be presented in any suitable form for such administration, for example in the form of tablets, capsules, powders, syrups or solutions or dispersions for injection. Preferably, and in accordance with the purpose of the present invention, the compound of the invention is administered in the form of a solid pharmaceutical entity, suitably as a tablet or a capsule or in the form of a suspension, solution or dispersion for injection.

Methods for the preparation of solid pharmaceutical preparations are well known in the art. Tablets may thus be prepared by mixing the active ingredients with ordinary adjuvants and/or diluents and subsequently compressing the mixture in a convenient tabletting machine. Examples of adjuvants or diluents comprise: corn starch, lactose, talcum, magnesium stearate, gelatine, lactose, gums, and the like. Any other adjuvant or additive such as colourings, aroma, preservatives, etc. may also be used provided that they are compatible with the active ingredients.

Furthermore, the compounds of this invention may exist in unsolvated as well as in solvated forms with pharmaceutically acceptable solvents such as water, ethanol, and the like. In general, the solvated forms are considered equivalent to the unsolvated forms for the purposes of this invention.

Some of the compounds of the present invention contain chiral centres and such compounds exist in the form of isomers (e.g. enantiomers). The invention includes all such isomers and any mixtures thereof including racemic mixtures.

Racemic forms can be resolved into the optical antipodes by known methods, for example by separation of diastereomeric salts thereof with an optically active acid and liberating the optically active amine compound by treatment with a base. Another method for resolving racemates into the optical antipodes is based upon chromatography on an optically active matrix. Racemic compounds of the present invention can thus be resolved into their optical antipodes, e.g. by fractional crystallisation of d- or l-(tartrates, mandelates or camphorsulphonate) salts for example. The compounds of the present invention may also be resolved by the formation of diastereomeric derivatives.

Additional methods for the resolution of optical isomers, known to those skilled in the art, may be used. Such methods include those discussed by J. Jaques, A. Collet, and S. Wilen in "Enantiomers, Racemates, and Resolutions", John Wiley and Sons, New York (1981).

Optically active compounds can also be prepared from optically active starting materials.

Definition of Substituents

Halogen means fluoro, chloro, bromo or iodo. Preferred halogens are F and Cl.

The term $C_{1-6}$-alkyl refers to a branched or unbranched alkyl group having from one to six carbon atoms inclusive, such as methyl, ethyl, 1-propyl, 2-propyl, 1-butyl, 2-butyl, 2-methyl-2-propyl and 2-methyl-1-propyl. Preferred alkyls are methyl and ethyl.

Similarly, $C_{2-6}$-alkenyl and $C_{2-6}$-alkynyl, respectively, designate such groups having from two to six carbon atoms, including one double bond and triple bond respectively, such as ethenyl, propenyl, butenyl, ethynyl, propynyl, and butynyl.

The term $C_{3-8}$-cycloalkyl designates a monocyclic or bicyclic carbocycle having three to eight C-atoms, such as cyclopropyl, cyclopentyl, cyclohexyl, etc.

The term $C_{3-8}$-cycloalkylalkyl designates a cycloalkyl as defined above and an alkyl as above.

The terms $C_{1-6}$-alkoxy and $C_{1-6}$-alkylthio designate such groups in which the alkyl group is $C_{1-6}$-alkyl as defined above.

The term aryl designates an aromatic hydrocarbon such as phenyl or naphtyl.

The term heteroaryl refers to a mono- or bicyclic heterocyclic aromatic group containing at least one N, S or O atom, such as furyl, pyrrolyl, thienyl, oxazolyl, isoxazolyl, thiazolyl, isothiazolyl, imidazolyl, pyridyl, pyrimidyl, tetrazolyl, benzofuranyl, benzothienyl, benzimidazolyl, indolyl. Preferred heteroaryls are monocyclic heteroaryls. Especially preferred is thienyl.

PREPARATORY EXAMPLES

The compounds of the invention may be prepared as follows:

1) alkylating an amine of formula II with an alkylating agent of formula I

G is a suitable leaving group such as e.g. halogen or mesylate.

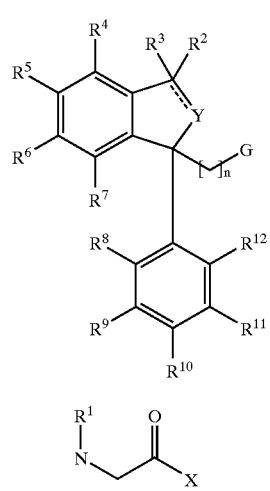

(I)

(II)

the substituents $R^1$–$R^{12}$, n, Y and X are as defined above;

2) alkylating an amine of formula III with an alkylating agent of formula IV

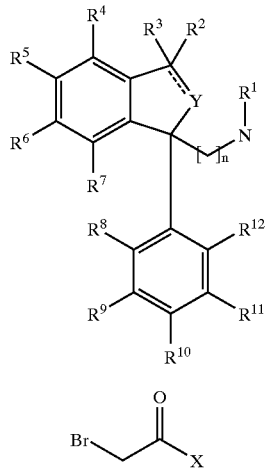

(III)

(IV)

wherein the substituents $R^1$–$R^{12}$, n, Y and X are as defined above;

3) Coupling of an aryl subsitituent of formula VI to the aryl bromide derivative of formula V wherein the substituents $R^4$–$R^7$ are halogens, $R^1$–$R^3$ and $R^8$–$R^{12}$, n, Y and X are as defined above

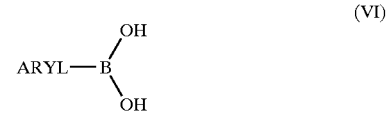

(VI)

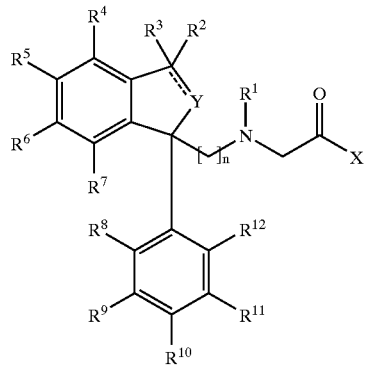

(V)

4) hydrolysing the ester group of a compound of formula VII to obtain the corresponding carboxylic acid derivative

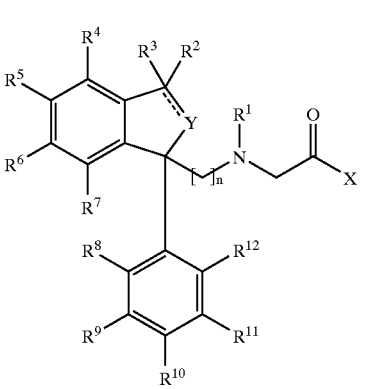

(VII)

the substituents $R^1$–$R^{12}$, n, and Y are as defined above and X is OH in the final product. The alkylations according to methods 1 and 2 are conveniently carried out in an inert solvent such as a suitably boiling alcohol or ketone or in tetrahydrofuran, preferably in the presence of an organic or inorganic base (potassium carbonate, diisopropylethylamine or triethylamine) at reflux temperature. Alternatively, the alkylation can be performed at a fixed temperature which is different from the boiling point in one of the above-mentioned solvents or in dimethylformamide, dimethylsulfoxide or N-methylpyrrolidin-2-one, preferably in the presence of a base.

Reagents of formula I are prepared by methods described in the literature, see. e.g. U.S. Pat. No. 3,549,656, GB 1166711 and Dykstra et al. *J. Med. Chem.* 1967, 10(3), 418–28.

Glycine derivatives of formula II are well described in the literature.

Amines of formula III are prepared as described by Bigler et. al. *Eur. J. Med. Chem.* 1977, 12, 289.

Biaryl derivatives of formula IV are prepared by suzuki type coupling of an aryl boronic acid with the desired halide in dimethoxyethane, tetrahydrofuran or toluene containing an inorganic base such as sodium carbonate and a palladium catalyst at a temperature between room temperature and the boiling point of the solvent.

The hydrolysis according to method 4 is conveniently performed in a suitably boiling alcohol in the presence of an aqueous base such as e.g. sodium hydroxide at ambient temperature. The starting materials of formula V are prepared by methods 1 or 2.

Experimental

Melting points were determined on a Büchi SMP-20 apparatus and are uncorrected. Analytical LC-MS data were obtained on a PE Sciex API 150EX instrument equipped with IonSpray source and Shimadzu LC-8A/SLC-10A LC system. The LC conditions (50×4.6 mm YMC ODS-A with 5 μm particle size) were linear gradient elution with water/acetonitrile/trifluoroacetic acid (90:10:0.05) to water/acetonitrile/trifluoroacetic acid (10:90:0.03) in 7 min at 2 mL/min. Purity was determined by integration of the UV trace (254 nm). The retention times, $R_t$, are expressed in minutes.

Mass spectra were obtained by an alternating scan method to give molecular weight information. The molecular ion, MH+, was obtained at low orifice voltage (5–20V) and fragmentation at high orifice voltage (100V).

Preparative LC-MS-separation was performed on the same instrument. The LC conditions (50×20 mm YMC ODS-A with 5 μm particle size) were linear gradient elution with water/acetonitrile/trifluoroacetic acid (80:20:0.05) to water/acetonitrile/trifluoroacetic acid (10:90:0.03) in 7 min at 22.7 mL/min. Fraction collection was performed by split-flow MS detection.

$^1$H NMR spectra were recorded at 500.13 MHz on a Bruker Avance DRX500 instrument or at 250.13 MHz on a Bruker AC 250 instrument. Deuterated chloroform (99.8%D) or dimethyl sulfoxide (99.9%D) were used as solvents. TMS was used as internal reference standard. Chemical shift values are expressed in ppm-values. The following abbreviations are used for multiplicity of NMR signals: s=singlet, d=doublet, t=triplet, q=quartet, qui=quintet, h=heptet, dd=double doublet, dt=double triplet, dq=double quartet, tt=triplet of triplets, m=multiplet, b=broad singlet. NMR signals corresponding to acidic protons are generally omitted. Content of water in crystalline compounds was determined by Karl Fischer titration. Standard workup procedures refer to extraction with the indicated organic solvent from proper aqueous solutions, drying of combined organic extracts (anhydrous $MgSO_4$ or $Na_2SO_4$), filtering and evaporation of the solvent in vacuo. For column chromatography, silica gel of type Kieselgel 60, 230–400 mesh ASTM was used. For ion-exchange chromatography, SCX, 1 g, Varian Mega Bond Elut®, Chrompack cat. No. 220776 was used. Prior use of the SCX-columns was pre-conditioned with 10% solution of acetic acid in methanol (3 mL).

The following examples will illustrate the invention further. They are, however, not to be construed as limiting.

Example 1

1a, N-(3-(5-Cyano-1-(4-fluorophenyl)-1,3-dihydroisobenzofuran-1-yl)-1-propyl)glycine.ethyl ester A stirred mixture of 3-(5-cyano-1-(4-fluorophenyl)-1,3-dihydroisobenzofuran-1-yl)-1-propyl amine (1.5 g), potassium carbonate (1.3 g) and ethanol (15 mL) was treated dropwise with a solution of ethyl bromoacetate (0.75 g) in ethanol (15 mL) at room temperature. After reflux for 1.5 h, the mixture was cooled and concentrated in vacuo. Standard work-up with ethyl acetate gave an oil which was purified by flash chromatography (eluent heptane/ethyl acetate/triethylamine 26:70:4). The title compound was obtained as a clear oil (0.77 g). LC/MS (m/z) 383 (MH+), purity (UV):>99%.

Example 2

2a, N-(3-(5-Cyano-1-(4-fluorophenyl)-1,3-dihydroisobenzofuran-1-yl)-1-propyl)-N-methylglycine.ethyl ester A stirred mixture of 3-(5-cyano-1-(4-fluorophenyl)-1,3-dihydroisobenzofuran-1-yl)-1-propyl iodide (3.1 g), ethyl N-methylglycinate (4.4 g) and diethylisopropylamine (4.4 g) in tetrahydrofuran (50 mL) was refluxed for 16 h. Standard work-up with ethyl acetate gave an oil which was purified by flash chromatography (eluent heptane/ethyl acetate/triethylamine 64:32:4) giving the title compound as a clear oil (1.4 g). LC/MS (m/z) 397 (MH+), purity (UV):>99%

Example 3

3a, N-(3-(5-Cyano-1-(4-fluorophenyl)-1,3-dihydroisobenzofuran-1-yl)-1-propyl)glycine hydrochloride A mixture of N-(3-(5-cyano-1-(4-fluorophenyl)-1,3-dihydroisobenzofuran-1-yl)-1-propyl)glycineethyl ester (0.7 g), methanol (6 mL) and 6 M sodium hydroxide (2 mL) was stirred at room temperature for 2 h. Adjustment of pH to <6.5 with dilute hydrochloric acid followed by standard work-up with ethyl acetate gave the title compound as an oil (0.2 g). LC/MS (m/z) 355 (MH+), purity (UV):>90%

In a similar manner, the following compound were prepared:

3b, N-(3-(5-Cyano-1-(4-fluorophenyl)-1,3-dihydroisobenzofuran-1-yl)-1-propyl)-N-methylglycine hydrochloride.

LC/MS (n/z) 369 (MH+), purity (UV):>90%

3c, Example 4

N-{3-[1-(3-chlorophenyl)-1,3-dihydroisobenzofuran-1-yl]-1-propyl}-N-methylglycine hydrochloride LC/MS (m/z) 360 (MH+), purity (UV 90%)

3d, Example 5

N-{3-[1-(3-trifluoromethylphenyl)-1,3-dihydroisobenzofuran-1-yl]-1-propyl}-N-methylglycine hydrochloride LC/MS (m/z) 394 (MH+), purity (UV 79%)

3e, Example 6

N-{3-[1-(3-trifluoromethylphenyl)-1,3-dihydroisobenzofuran-1-yl]-1-propyl}-N-methyl(1-ethyl) glycine hydrochloride LC/MS (m/z) 422 (MH+), purity (UV 79%)
3f, Example 7
N-{3-[1-(4-methylphenyl)-1,3-dihydroisobenzofuran-1-yl]-1-propyl}-N-methylglycine. hydrochloride
LC/MS (m/z) 378 (MH+), purity (UV 91%)
3g, Example 8
N-{3-[1-(4-fluorophenyl)-1,3-dihydroisobenzofuran-1-yl]-1-propyl}-N-methylglycine hydrochloride
LC/MS (m/z) 344 (MH+), purity (UV 81%)
3h, Example 9
N-{3-[1-(4-fluorophenyl)-1,3-dihydroisobenzofuran-1-yl]-1-propyl}-N-methylalanine hydrochloride
LC/MS (m/z) 358 (MH+), purity (UV 81%)
3i, Example 10
N-{3-[1-(4-fluorophenyl)-1,3-dihydroisobenzofuran-1-yl]-1-propyl}-N-methyl(1-ethyl)glycine hydrochloride
LC/MS (m/z) 372 (MH+), purity (UV 86%)
3j, Example 11
N-{3-[4-chloro-1-(3-methyl-4-fluorophenyl)-1,3-dihydroisobenzofuran-1-yl]-1-propyl}-methylglycine hydrochloride.
LC/MS (m/z) 392 (MH+), purity (UV 86%)
3k, Example 12
N-{3-[4-chloro-1-(4-chlorophenyl)-1,3-dihydroisobenzofuran-1-yl]-1-propyl}-N-methylglycine hydrochloride.
LC/MS (m/z) 394 (MH+), purity (UV 98%)
3l, Example 13
N-{3-[5-chloro-1-(4-chlorophenyl)-1,3-dihydroisobenzofuran-1-yl]-1-propyl}-N-methylalanine hydrochloride
LC/MS (m/z) 408 (MH+), purity (UV 85%)
3m, Example 14
N-{3-[6-chloro-1-(4-chlorophenyl)-1,3-dihydroisobenzofuran-1-yl]-1-propyl}-N-methylglycine hydrochloride.
LC/MS (m/z) 394 (MH+), purity (UV 99%)
3n, Example 15
N-{3-[6-chloro-1-(4-methylphenyl)-1,3-dihydroisobenzofuran-1-yl]-1-propyl}-N-methylglycine hydrochloride.
LC/MS (m/z) 374 (MH+), purity (UV 76%)
3o, Example 16
N-{3-[6-chloro-1-(4-methoxyphenyl)-1,3-dihydroisobenzofuran-1-yl]-1-propyl}-N-methylglycine hydrochloride
LC/MS (m/z) 390 (MH+), purity (UV 98%).
3p, Example 17
N-{3-[5-fluoro-1-(4-chlorophenyl)-1,3-dihydroisobenzofuran-1-yl]-1-propyl}-N-methylglycine hydrochloride.
LC/MS (m/z) 378 (MH+), purity (UV 85%).
3q, Example 18
N-{3-[5-fluoro-1-(4-methoxyphenyl)-1,3-dihydroisobenzofuran-1-yl]-1-propyl}-N-methylglycine hydrochloride.
LC/MS (m/z) 378 (MH+), purity (UV 99%).
3r, Example 19
N-{3-[5-trifluoromethyl-1-(4-fluorophenyl)-1,3-dihydroisobenzofuran-1-yl]-1-propyl}-N-methylglycine hydrochloride
LC/MS (m/z) 412 (MH+), purity (UV 81%)
3s, Example 20
N-{3-[5-trifluoromethyl-1-(4-fluorophenyl)-1,3-dihydroisobenzofuran-1-yl]-1-propyl}-N-methylalanine hydrochloride
LC/MS (m/z) 426 (MH+), purity (UV 98%).
3t, Example 21
N-{3-[5-cyano-1-(3-methyl-4-fluorophenyl)-1,3-dihydroisobenzofuran-1-yl]-1-propyl}-N-methylglycine hydrochloride.

LC/MS (m/z) 383 (MH+), purity (UV 83%).
3u, Example 22
N-{3-[5-cyano-1-(4-cyanophenyl)-indan-1-yl]-1-propyl}-N-methylalanine hydrochloride.
LC/MS (m/z) 388 (MH+), purity (80%).
3v, Example 23
N-{3-[5-cyano-1-(4-methoxyphenyl)-1,3-dihydroisobenzofuran-1-yl]-1-propyl}-N-methylglycine hydrochloride
LC/MS (m/z) 381 (MH+), purity (UV 81%).
3x, Example 24
N-{3-[5-cyano-1-(4-fluorophenyl)-1,3-dihydroisobenzofuran-1-yl]-1-propyl}-N-methylglycine hydrochloride.
LC/MS (m/z) 369 (MH+), purity (UV 98%)
3y, Example 95
N-{2-[5-cyano-1-(4-fluorophenyl)-1,3-dihydroisobenzofuran-1-yl]ethyl}-N-methylglycine hydrochloride.
LC/MS (m/z) 355 (MH+), purity (UV 94%)
3z, Example 26
N-{3-[5-Chloro-1-(4-chloro-phenyl)-indan-1-yl]-propyl}-N-methylglycine hydrochloride
LC/MS (m/z) 392 (MH+), purity (UV 98%)
3aa, Example 27
N-{3-[5-Chloro-1-(4-chloro-phenyl)-indan-1-yl]-propyl}-N-methylalanine hydrochloride
LC/MS (m/z) 406 (MH+), purity (UV 95%)
3ab, Example 28
N-{3-[3-spirocyclopentyl-1-(4-methylphenyl)-1,3-dihydroisobenzofuran-1-yl]-1-propyl}-N-methylglycine hydrochloride
3ac, Example 29
N-[3-(3,3-Dimethyl-1-phenyl-1,3-dihydro-benzo[c]thiophen-1-yl)-propyl]-N-methylglycine hydrochloride
3ad, Example 30
N-[3-(3,3-Dimethyl-1-phenyl-1,3-dihydro-benzo[c]thiophen-1-yl)-propyl]-N-methylalanine
LC/MS (m/z) 370 purity (UV 96%)
3ae, Example 32
N-{3-[5-Bromo-1-(4-chlorophenyl)-1,3-dihydroisobenzofuran-1-yl]-1-propyl}-N-methylglycine
LC/MS (m/z) 440 (MH+), purity (ELSD 93%)
3af, Example 33
N-{2-[1-(4-Chloro-phenyl)-3,3-dimethyl-1,3-dihydro-isobenzofuran-1-yl]-ethyl}-N-methylglycine
LC/MS (m/z) 374 (MH+), purity (UV 72%)
3ag, Example 34
N-[3-(3-methyl-1-phenyl-1H-inden-1-yl)-propyl]-N-methylglycine
LC/MS (m/z) 336 (MH+), purity (UV 85%)
3ah, Example 35
N-[3-(5-Chloro-1-thiophen-2-yl-1,3-dihydro-isobenzofuran-1-yl)-propyl]-N-methylalanine
LC/MS (m/z) 380 (MH+), purity (UV 85%)
3ai, Example 36
N-[3-(5-Chloro-1-thiophen-2-yl-1,3-dihydro-isobenzofuran-1-yl)-propyl]-N-methyl(1-ethyl)-glycine
LC/MS (m/z) 394 (MH+), purity (UV 80%)
3aj, Example 37
N-[3-(3-methyl-1-phenyl-1,3-dihydro-isobenzofuran-1-yl)-propyl]-N-methylalanine
LC/MS (m/z) 354 (MH+), purity (UV 78%)
3ak, Example 38
N-[2-(3-methyl-1-phenyl-indan-1-yl)-ethyl]-amino}-N-methyl alanine
LC/MS (m/z) 451, purity (UV 92%)
3al, Example 39
N-{3-[1-(4-Chloro-phenyl)-5-(4-methyl-phenyl)-1,3-dihydro-isobenzofuran-1-yl]-ethyl}-N-methyl-glycine Example 4

4a, N-{3-[5-Bromo-chloro-1-(4-chlorophenyl)-1,3-dihydroisobenzofuran-1-yl]-1-ethyl}-N-methylglycine ethyl ester (226 mg, 0.5 mmol) was dissolved in a 1:1 mixture of tetrahydrofuran and dimethoxyethane (3 mL) containing tetrakis (triphenylphosphine)palladium under nitrogen. To the reaction was added 4-chlorophenyl boronic acid (102 mg, 0.75 mmol) and 0.5M aqueous sodium carbonate solution (2 mL, 1 mmol) and the reaction was heated to 65° C. for 18 hours. The solution was diluted with water (5 mL) and ethyl acetate (7 mL). The organic layer was separated and the aqueous layer was re-extracted with ethyl acetate (5 mL). The organic extractions were combined and washed with saturated brine solution (7 mL) before being evaporated in the presence of 1 g of silica gel. The crude product absorbed on silica gel was poured on top of a 20 g silica gel cartridge and eluted with a gradient solvent system eluting from heptane to heptane/ethyl acatet (1:1) over 37 minutes. The product was isolated as a light oil (135 mg, 64%). LC/MS 479.

The compound was hydrolysed as described for Experimental 3a to give the N-methyglycine hydrochloride derivative.

LC/MS (m/z) 436, purity (UV 92%)

In an analogous fashion, the following compounds were prepared:

4b, Example 40

N-{3-[1-(4-Chloro-phenyl)-5-(4-methoxy-phenyl)-1,3-dihydro-isobenzofuran-1-yl]-ethyl}-N-methyl-glycine LC/MS (m/z) 452, purity (UV 94%)

4c, Example 41

N-{3-[1-(4-Chloro-phenyl)-5-(2-thiophenyl)-1,3-dihydro-isobenzofuran-1-yl]-ethyl}-N-methyl-glycine LC/MS (m/z) 428, purity (UV 96%)

4d, Example 42

N-{3-[1-(4-Chloro-phenyl)-5-(4-methyl-phenyl)-1,3-dihydro-isobenzofuran-1-yl]-propyl}-N-methyl-glycine LC/MS (m/z) 450, purity 91%

4e, Example 43

N-{3-[1-(4-Chloro-phenyl)-5-(4-methoxy-phenyl)-1,3-dihydro-isobenzofuran-1-yl]-propyl}-N-methyl-glycine LC/MS (m/z) 466, purity (UV 95%)

4f, Example 44

N-{3-[1-(4-chloro-phenyl)-5-(4-trifluoromethyl-phenyl)-1,3-dihydro-isobenzofuran-1-yl]-propyl}-N-methyl-glycine LC/MS (m/z) 504, purity (UV 89%)

4g, Example 45

N-{3-[1-(4-Chloro-phenyl)-5-(4-chloro-phenyl)-1,3-dihydro-isobenzofuran-1-yl]-ethyl}-N-methyl-glycine LC/MS (m/z) 456, purity 96%

4h, Example 46

N-{2-[1-(4-Chloro-phenyl)-5-(5-chloro-thiophen-2-yl)-1,3-dihydro-isobenzofuran-1-yl]-ethyl}-N-methyl-glycine LC/MS (m/z) 462, purity 74%

4i, Example 47

N-{3-[1-(4-Chloro-phenyl)-5-(3-methyl-phenyl)-1,3-dihydro-isobenzofuran-1-yl]-ethyl}-N-methyl-glycine LC/MS (m/z) 436, purity UV 94%

4j, Example 48

N-{3-[1-(4-Chloro-phenyl)-5-(2-methyl-phenyl)-1,3-dihydro-isobenzofuran-1-yl]-ethyl}-N-methyl-glycine LC/MS (m/z) 436, purity (UV 91%)

4k, Example 49

N-{3-[1-(4-Chloro-phenyl)-5-(2,5-dichloro-phenyl)-1,3-dihydro-isobenzofuran-1-yl]-ethyl}-N-methyl-glycine LC/MS (m/z) 490, purity 94%

4l, Example 50

N-{3-[1-(4-chloro-phenyl)-5-(3-trifluoromethyl-phenyl)-1,3-dihydro-isobenzofuran-1-yl]-ethyl}-N-methyl-glycine LC/MS (m/z) 490, purity 89%

4m, Example 51

N-{3-[1-(4-chloro-phenyl)-5-(3-trifluoromethyl-phenyl)-1,3-dihydro-isobenzofuran-1-yl]-propyl}-N-methyl-glycine LC/MS (m/z) 506, purity 91%

4n, Example 52

N-{3-[1-(4-Chloro-phenyl)-5-(3,4-dichloro-phenyl)-1,3-dihydro-isobenzofuran-1-yl]-ethyl}-N-methyl-glycine LC/MS (m/z) 490, purity 89%

4o, Example 53

N-{3-[1-(4-Chloro-phenyl)-5-(4-chloro-phenyl)-1,3-dihydro-isobenzofuran-1-yl]-propyl}-N-methyl-glycine LC/MS (m/z) 470, purity (UV 94%)

4p, Example 54

N-{3-[1-(4-Chloro-phenyl)-5-(3-methyl-phenyl)-1,3-dihydro-isobenzofuran-1-yl]-propyl}-N-methyl-glycine LC/MS (m/z) 450, purity 96%

4q, Example 55

N-{3-[1-(4-Chloro-phenyl)-5-(2-methyl-phenyl)-1,3-dihydro-isobenzofuran-1-yl]-propyl}-N-methyl-glycine LC/MS (m/z) 450, purity 93%

4r, Example 56

N-{3-[1-(4-Chloro-phenyl)-5-(2,5-dichloro-phenyl)-1,3-dihydro-isobenzofuran-1-yl]-propyl}-N-methyl-glycine LC/MS (m/z) 506, purity 91%

4s, Example 57

N-{3-[1-(4-Chloro-phenyl)-5-(3,4-dichloro-phenyl)-1,3-dihydro-isobenzofuran-1-yl]-propyl}-N-methyl-glycine LC/MS (m/z) 504, purity 95%

4t, Example 58

N-{3-[1-(4-chloro-phenyl)-5-(2-trifluoromethyl-phenyl)-1,3-dihydro-isobenzofuran-1-yl]-propyl}-N-methyl-glycine LC/MS (m/z) 504, purity 78%

Pharmacological Testing

The compounds of the invention were tested in a well-recognised and reliable test measuring glycine uptake:

[$^3$H]-Glycine Uptake

Cells transfected with the human GlyT-1b were seeded in 96 well plates. Prior to the experiment the cells were washed twice in HBS (10 mM Hepes-tris (pH 7.4), 2.5 mM KCl, 1 mM $CaCl_2$, 2.5 mM $MgSO_4$,) and pre-incubated with test compound for 6 minutes. Afterwards, 10 nM $^3$H-glycine was added to each well and the incubation was continued for 15 minutes. The cells were washed twice in HBS. Scintillation fluid was added and the Plates were counted on a Trilux (Wallac) scintillation counter.

The test results were as follows:

Inhibition of Glycine Transport by hGlyT-

| Compound | Compound Name | $IC_{50}$ GlyT-1b |
|---|---|---|
| 3f | N-{3-[1-(4-methylphenyl)-1,3-dihydroisobenzofuran-1-yl]-1-propyl}-N-methylglycine. | 5400 |
| 3k | N-{3-[4-chloro-1-(4-chlorophenyl)-1,3-dihydroisobenzofuran-1-yl]-1-propyl}-N-methylglycine. | 4100 |
| 3l | N-{3-[5-chloro-1-(4-chlorophenyl)-1,3-dihydroisobenzofuran-1-yl]-1-propyl}-N-methylalanine | 5500 |
| 3m | N-{3-[6-chloro-1-(4-chlorophenyl)-1,3-dihydroisobenzofuran-1-yl]-1-propyl}-N-methylglycine. | 7200 |
| 3n | N-{3-[6-chloro-1-(4-methylphenyl)-1,3-dihydroisobenzofuran-1-yl]-1-propyl}-N-methylglycine. | 9600 |
| 3t | N-{3-[5-cyano-1-(3-methyl-4-fluorophenyl)-1,3-dihydroisobenzofuran-1-yl]-1-propyl}-N-methylglycine. | 5700 |
| 3v | N-{3-[5-cyano-1-(4-methoxyphenyl)-1,3-dihydroisobenzofuran-1-yl]-1-propyl}-N-methylglycine | 8600 |
| 3z | N-{3-[5-Chloro-1-(4-chloro-phenyl)-indan-1-yl]-propyl}-N-methylglycine | 1100 |
| 3aa | N-{3-[5-Chloro-1-(4-chloro-phenyl)-indan-1-yl]-propyl}-N-methylalanine | 470 |
| 3ae | N-{3-[5-Bromo-1-(4-chlorophenyl)-1,3-dihydroisobenzofuran-1-yl]-1-propyl}-N-methylglycine | 4000 |
| 3af | N-{2-[1-(4-Chloro-phenyl)-3,3-dimethyl-1,3-dihydro-isobenzofuran-1-yl]-ethyl}-N-methylglycine | 3500 |
| 3ak | N-[2-(3-methyl-1-phenyl-indan-1-yl)-ethyl]-amino}-N-methyl alanine | 2200 |
| 3al | N-{3-[1-(4-Chloro-phenyl)-5-(4-methyl-phenyl)-1,3-dihydro-isobenzofuran-1-yl]-ethyl}-N-methyl-glycine | 2200 |
| 4c | N-{3-[1-(4-Chloro-phenyl)-5-(2-thiophenyl)-1,3-dihydro-isobenzofuran-1-yl]-ethyl}-N-methyl-glycine | 1200 |
| 4d | N-{3-[1-(4-Chloro-phenyl)-5-(4-methyl-phenyl)-1,3-dihydro-isobenzofuran-1-yl]-propyl}-N-methyl-glycine | 1500 |
| 4j | N-{3-[1-(4-Chloro-phenyl)-5-(2-methyl-phenyl)-1,3-dihydro-isobenzofuran-1-yl]-ethyl}-N-methyl-glycine | 710 |
| 4k | N-{3-[1-(4-Chloro-phenyl)-5-(2,5-dichloro-phenyl)-1,3-dihydro-isobenzofuran-1-yl]-ethyl}-N-methyl-glycine | 950 |

The above results demonstrate that the compounds of the invention are able to inhibit glycine uptake into synaptosomes in micromolar concentrations.

What is claimed is:

1. A compound represented by the formula I:

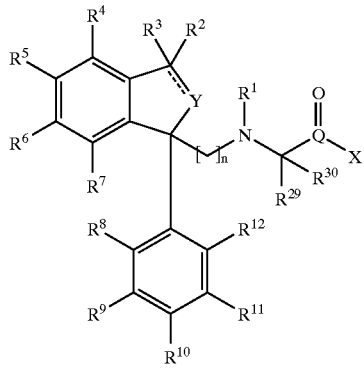

wherein
$R^1$ is hydrogen, $C_{1-6}$-alkyl, cycloalkyl or cycloalkylalkyl;
$R^2$ and $R^3$ are independently hydrogen, halogen, $C_{1-6}$-alkyl, $C_{3-8}$ cycloalkyl or $C_{3-8}$ cycloalkyl-$C_{1-6}$-alkyl or $R^2$ and $R^3$ together form a $C_{3-8}$ cycloalkyl;
$R^4$, $R^5$, $R^6$ and $R^7$ are independently hydrogen, halogen, $CF_3$, $NO_2$, CN, $C_{1-6}$ alkyl, $C_{2-6}$ alkenyl, $C_{2-6}$ alkynyl, $C_{3-8}$ cycloalkyl, $C_{1-6}$ alkoxy, $C_{1-6}$ alkylthio, OH, SH, $NR^{14}R^{15}$, wherein $R^{14}$ and $R^{15}$ are independently hydrogen or $C_{1-6}$-alkyl; $-COR^{16}$ wherein $R^{16}$ is OH, $C_{1-6}$ alkyl, $C_{1-6}$-alkoxy, $NR^{17}R^{18}$, wherein $R^{17}$ and $R^{18}$ are independently hydrogen or $C_{1-6}$-alkyl; aryl or heteroaryl, wherein aryl and heteroaryl are optionally substituted one or more times with halogen, $CF_3$, $OCF_3$, CN, $NO_2$, $C_{1-6}$ alkyl, $C_{2-6}$ alkenyl, $C_{2-6}$ alkynyl, $C_{3-8}$ cycloalkyl, $C_{1-6}$ alkoxy, $C_{1-6}$ thioalkyl, OH, SH or $NR^{24}R^{25}$, wherein $R^{24}$ and $R^{25}$ are independently hydrogen or $C_{1-6}$ alkyl; or $R^4$ and $R^5$, or $R^5$ and $R^6$, or $R^6$ and $R^7$ together form a fused, aromatic, saturated or partly saturated ring which optionally contains one or more heteroatoms O, N or S;

$R^8$, $R^9$, $R^{10}$, $R^{11}$, and $R^{12}$ are independently hydrogen, halogen, $CF_3$, $OCF_3$, CN, $NO_2$, $C_{1-6}$ alkyl, $C_{2-6}$ alkenyl, $C_{2-6}$ alkynyl, $C_{3-8}$ cycloalkyl, $C_{1-6}$ alkoxy, $C_{1-6}$ alkylthio, OH, SH, $NR^{19}R^{20}$, wherein $R^{19}$ and $R^{20}$ are independently hydrogen or $C_{1-6}$ alkyl; or $R^8$, $R^9$, $R^{10}$, $R^{11}$ and $R^{12}$ are independently $-COR^{21}$, wherein $R^{21}$ represents OH, $C_{1-6}$ alkoxy, $NR^{22}R^{23}$ wherein $R^{22}$ and $R^{23}$ are independently hydrogen or $C_{1-6}$-alkyl; or $R^8$, $R^9$, $R^{10}$, $R^{11}$ and $R^{12}$ are independently aryl or heteroaryl, wherein aryl and heteroaryl are optionally substituted one or more times with halogen, $CF_3$, $OCF_3$, CN, $NO_2$, $C_{1-6}$ alkyl, $C_{2-6}$ alkenyl, $C_{2-6}$ alkynyl, $C_{3-8}$ cycloalkyl, $C_{1-6}$ alkoxy, $C_{1-6}$ alkylthio, OH, SH, $COR^{26}$, wherein $R^{26}$ is OH, $C_{1-6}$ alkoxy or $C_{1-6}$ alkyl; or $NR^{30}R^{31}$, wherein $R^{30}$ and $R^{31}$ are independently hydrogen or $C_{1-6}$ alkyl;

$R^8$ and $R^9$, or $R^9$ and $R^{10}$, or $R^{10}$ and $R^{11}$ or $R^{11}$ and $R^{12}$ together form a fused, aromatic, saturated or partly saturated ring which optionally contains one or more heteroatoms O, N or S;

Y is O, S, $CH_2$ or CH, and when Y is CH then the dotted line is a bond;

n is 2, 3, 4, 5 or 6;

Q represents C, P—$OR^{29}$ or S=O, wherein $R^{29}$ represents hydrogen or $C_{1-6}$-alkyl;

X is $OR^{13}$ or $NR^{27}R^{28}$, wherein $R^{13}$, $R^{27}$, and $R^{28}$ are independently hydrogen, $C_{1-6}$-alkyl, aryl or aryl-$C_{1-6}$-alkyl, wherein aryl may be substituted with halogen, $CF_3$, $OCF_3$, CN, $NO_2$, or $C_{1-6}$-alkyl, optionally $R^{27}$ and $R^{28}$ together form a ring which may contain further nitrogen, oxygen or sulfur atoms and the ring may optionally be partly saturated, $R^{29}$ and $R^{30}$ represent hydrogen, $C_{1-6}$-alkyl, cycloalkyl or cycloalkylalkyl; or a pharmaceutically acceptable addition salt thereof.

2. The compound according to claim 1, wherein n is 2 or 3.

3. The compound according to claim 1, wherein $R^1$ is $CH_3$.

4. The compound according to claim 1, wherein Q is C.

5. The compound according to claim 1, wherein X is OH or $C_{1-6}$-alkoxy.

6. The compound according to claim 1, wherein $R^7$ is hydrogen, and $R^4$, $R^5$ or $R^6$ is hydrogen, $C_{1-6}$-alkyl, CN, halogen, $CF_3$ or phenyl optionally substituted one or more times with halogen, $C_{1-6}$-alkyl, CN, halogen, $CF_3$ or phenyl optionally substituted one or more times with halogen, $C_{1-6}$-alkyl, $C_{1-6}$-alkoxy, $CF_3$, or $R^4$, $R^5$ or $R^6$ is heteroaryl optionally substituted one or more times with halogen or wherein $R^4$ and $R^5$, or $R^5$ and $R^6$ together form a fused aryl.

7. The compound according to claim 1 wherein $R^8$, $R^9$, $R^{10}$, $R^{11}$ or $R^{12}$ is independently hydrogen, halogen, alkyl, alkoxy, or $R^8$ and $R^9$, or $R^9$ and $R^{10}$ together form a fused aryl.

8. The compound according to claim 1 where $R^8$, $R^9$, $R^{10}$, $R^{11}$ or $R^{12}$ independently are halogen, $C_{1-6}$-alkyl, $C_{1-6}$-alkoxy.

9. A pharmaceutical composition comprising one or more compounds of claim 1, or a pharmaceutically acceptable acid addition salt thereof in a therapeutically effective amount and in combination with one or more pharmaceutically acceptable carriers or diluents.

10. A method for the treatment of a disease or condition selected from the group consisting of psychoses, dementia, and pain, said method comprising administering to a patient in need thereof, an effective amount of a compound according to claim 1 to treat said disease or condition.

11. The method of claim 10 which comprises administering said compound to treat schizophrenia.

12. The method of claim 11 which comprises administering said compound to treat the positive symptoms of schizophrenia.

13. The method of claim 11 which comprises administering said compound to treat the negative symptoms of schizophrenia.

14. The method of claim 10 wherein said disease or condition is responsive to modulation of the glycine transporter.

15. The method of claim 14 wherein said disease or condition is responsive to antagonism of the glycine transporter.

16. A method for improving cognition in a condition where the cognitive processes are diminished, said method comprising administering to a patient in need thereof, an effective amount of a compound according to claim 1 to improve cognition in said patient.

17. The method of claim 16 wherein said condition is selected from the group consisting of Alzheimer's disease, multi-infarct dementia, AIDS dementia, Huntington's disease, Parkinson's disease, amyotrophic lateral sclerosis and diseases wherein the brain is damaged by inner or outer influence.

18. The method of claim 17 wherein the brain is damaged by trauma to the head or stroke.

19. The method of claim 16 wherein said disease or condition is responsive to modulation of the glycine transporter.

20. The method of claim 19 wherein said disease or condition is responsive to antagonism of the glycine transporter.

* * * * *

UNITED STATES PATENT AND TRADEMARK OFFICE
CERTIFICATE OF CORRECTION

PATENT NO. : 6,921,774 B2
DATED : July 26, 2005
INVENTOR(S) : Ejner K. Moltzen et al.

It is certified that error appears in the above-identified patent and that said Letters Patent is hereby corrected as shown below:

<u>Title page,</u>
Item [75], Inventors, please delete "Paul Garrick Smith" and substitute -- Garrick Paul Smith --.

Signed and Sealed this

Fourth Day of October, 2005

JON W. DUDAS
*Director of the United States Patent and Trademark Office*